United States Patent [19]

Bundy

[11] 4,144,276

[45] Mar. 13, 1979

[54] 3,7-INTER-PHENYLENE-4,5,6-TRINOR-3-OXA-2-DECARBOXY-2-HYDROXYMETHYL-9-DEOXY-9-METHYLENE-PGF-TYPE COMPOUNDS

[75] Inventor: Gordon L. Bundy, Portage, Mich.

[73] Assignee: The Upjohn Company, Kalamazoo, Mich.

[21] Appl. No.: 904,189

[22] Filed: May 8, 1978

Related U.S. Application Data

[60] Division of Ser. No. 832,239, Sep. 12, 1977, which is a division of Ser. No. 682,848, May 4, 1976, Pat. No. 4,060,534, which is a continuation-in-part of Ser. No. 651,622, Jan. 23, 1976, Pat. No. 4,021,467, which is a division of Ser. No. 556,768, Mar. 10, 1975, Pat. No. 3,950,363.

[51] Int. Cl.$^2$ ............................................. C07C 177/00
[52] U.S. Cl. .................................... 568/645; 568/646
[58] Field of Search ................................... 260/613 D

[56] References Cited

U.S. PATENT DOCUMENTS 3,931,299  1/1976  Strike ................................... 560/121

*Primary Examiner*—Gerald A. Schwartz
*Attorney, Agent, or Firm*—Robert A. Armitage

[57] ABSTRACT

This invention comprises certain analogs PGE or 11-deoxy-PGE compounds in which the carbonyl at C-9 is replaced by methylene. Also provided in this invention, are novel chemical processes and novel chemical intermediates useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

1 Claim, No Drawings

3,7-INTER-PHENYLENE-4,5,6-TRINOR-3-OXA-2-DECARBOXY-2-HYDROXYMETHYL-9-DEOXY-9-METHYLENE-PGF-TYPE COMPOUNDS

The present application is a divisional application of Ser. No. 832,239, filed Sept. 12, 1977, now pending; which is a divisional application of Ser. No. 682,848, filed May 4, 1976, now issued as U.S. Pat. No. 4,060,534 on Nov. 29, 1977; which is a continuation-in-part of Ser. No. 651,622, filed Jan. 23, 1976, issued as U.S. Pat. No. 4,021,467 on May 3, 1977; which is a division of Ser. No. 556,768, filed Mar. 10, 1975, issued as U.S. Pat. No. 3,950,363 on Apr. 13, 1976.

The present invention relates to prostaglandin analogs, for which the essential material constituting disclosure thereof is incorporated by reference here from Ser. No. 682,848, now U.S. Pat. No. 4,060,534.

I claim:

1. A prostaglandin analog of the formula

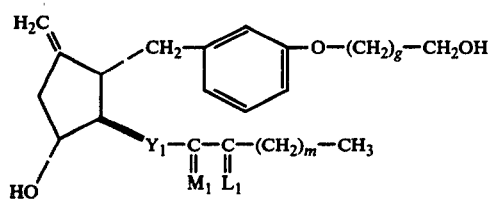

wherein $Y_1$ is trans—CH=CH—, —C≡C—, or —CH$_2$CH$_2$—;
wherein $M_1$ is

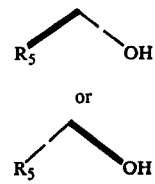

wherein $R_5$ is hydrogen or methyl;
wherein $L_1$ is

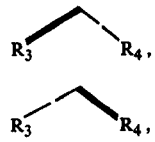

or a mixture of

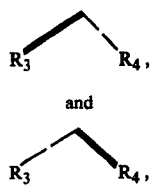

wherein $R_3$ and $R_4$ are hydrogen, methyl, or fluoro, being the same or different, with the proviso that one of $R_3$ and $R_4$ is fluoro only when the other is hydrogen or fluoro;
wherein g is one, 2, or 3; and
wherein m is one to 5, inclusive.

* * * * *